(12) United States Patent
Swogger et al.

(10) Patent No.: US 10,414,656 B2
(45) Date of Patent: *Sep. 17, 2019

(54) DISCRETE CARBON NANOTUBES WITH TARGETED OXIDATION LEVELS AND FORMULATIONS THEREOF

(71) Applicant: MOLECULAR REBAR DESIGN, LLC, Austin, TX (US)

(72) Inventors: Kurt W. Swogger, Austin, TX (US); Clive P. Bosnyak, Dripping Springs, TX (US); Nancy Henderson, Austin, TX (US); Malcolm Finlayson, Houston, TX (US); Bryce Daniel Sturtevant, Austin, TX (US); Steve Hoenig, Austin, TX (US)

(73) Assignee: Molecular Rebar Design, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/092,130

(22) PCT Filed: Apr. 7, 2017

(86) PCT No.: PCT/US2017/026655
§ 371 (c)(1),
(2) Date: Oct. 8, 2018

(87) PCT Pub. No.: WO2017/177166
PCT Pub. Date: Oct. 12, 2017

(65) Prior Publication Data
US 2019/0161350 A1 May 30, 2019

Related U.S. Application Data

(60) Provisional application No. 62/319,599, filed on Apr. 7, 2016.

(51) Int. Cl.
| | | |
|---|---|---|
| *C01B 32/168* | (2017.01) |
| *A61K 9/00* | (2006.01) |
| *A61K 47/02* | (2006.01) |
| *C02F 1/28* | (2006.01) |
| *C01B 32/174* | (2017.01) |
| *C01B 32/178* | (2017.01) |
| *C01B 32/16* | (2017.01) |
| *A61P 25/28* | (2006.01) |
| *A61L 27/08* | (2006.01) |
| *A61L 27/36* | (2006.01) |
| *A61L 27/38* | (2006.01) |
| *C12N 5/0797* | (2010.01) |
| *C08K 3/04* | (2006.01) |
| *C08K 7/24* | (2006.01) |
| *B82Y 30/00* | (2011.01) |
| *B82Y 40/00* | (2011.01) |
| *C02F 103/06* | (2006.01) |
| *C02F 101/30* | (2006.01) |
| *C02F 101/36* | (2006.01) |
| *B82Y 5/00* | (2011.01) |
| *B82Y 35/00* | (2011.01) |

(52) U.S. Cl.
CPC .......... *C01B 32/168* (2017.08); *A61K 9/0092* (2013.01); *A61K 47/02* (2013.01); *A61L 27/08* (2013.01); *A61L 27/3675* (2013.01); *A61L 27/3804* (2013.01); *A61P 25/28* (2018.01); *C01B 32/16* (2017.08); *C01B 32/174* (2017.08); *C01B 32/178* (2017.08); *C02F 1/283* (2013.01); *C08K 3/04* (2013.01); *C08K 7/24* (2013.01); *C12N 5/0623* (2013.01); *A61K 9/0019* (2013.01); *B82Y 5/00* (2013.01); *B82Y 30/00* (2013.01); *B82Y 35/00* (2013.01); *B82Y 40/00* (2013.01); *C01B 2202/06* (2013.01); *C01B 2202/34* (2013.01); *C01B 2202/36* (2013.01); *C02F 2101/30* (2013.01); *C02F 2101/36* (2013.01); *C02F 2103/06* (2013.01); *C02F 2305/08* (2013.01); *Y10S 977/744* (2013.01); *Y10S 977/748* (2013.01); *Y10S 977/752* (2013.01); *Y10S 977/846* (2013.01); *Y10S 977/847* (2013.01); *Y10S 977/903* (2013.01); *Y10S 977/906* (2013.01)

(58) Field of Classification Search
None
See application file for complete search history.

(56) References Cited

U.S. PATENT DOCUMENTS

| | | |
|---|---|---|
| 2006/0239891 A1 | 10/2006 | Niu et al. |
| 2012/0183770 A1 | 7/2012 | Bosnyak et al. |
| 2012/0238725 A1 | 9/2012 | Elghanian et al. |
| 2015/0238476 A1 | 8/2015 | Bosnyak et al. |

OTHER PUBLICATIONS

Cao et al.; Preparation and Properties of Plasticized Starch/Multiwalled Carbon Nanotubes Composites; Journal of Applied Polymer Science; Jul. 12, 2007.*

* cited by examiner

*Primary Examiner* — Guinever S Gregorio
(74) *Attorney, Agent, or Firm* — Stephen P. Krupp

(57) ABSTRACT

Discrete, individualized carbon nanotubes having targeted, or selective, oxidation levels and/or content on the interior and exterior of the tube walls are claimed. Such carbon nanotubes can have little to no inner tube surface oxidation, or differing amounts and/or types of oxidation between the tubes' inner and outer surfaces. These new discrete carbon nanotubes are useful in plasticizers, which can then be used as an additive in compounding and formulation of elastomeric, thermoplastic and thermoset composite for improvement of mechanical, electrical and thermal properties.

12 Claims, No Drawings

DISCRETE CARBON NANOTUBES WITH TARGETED OXIDATION LEVELS AND FORMULATIONS THEREOF

CROSS REFERENCE TO RELATED APPLICATIONS

This application is related to U.S. Ser. No. 13/164,456, filed Jun. 20, 2011, and its progeny; and U.S. Ser. No. 13/140,029, filed Aug. 9, 2011, and its progeny, the disclosures of each of which is incorporated herein by reference. This application claims priority to U.S. Provisional Application No. 62/319,599, filed Apr. 7, 2016.

FIELD OF INVENTION

The present invention is directed to novel discrete carbon nanotube compositions having targeted oxidation levels and/or content, and formulations thereof, such as with plasticizers.

BACKGROUND AND SUMMARY OF THE INVENTION

Carbon nanotubes can be classified by the number of walls in the tube, single-wall, double wall and multiwall. Carbon nanotubes are currently manufactured as agglomerated nanotube balls, bundles or forests attached to substrates. Use of carbon nanotubes as a reinforcing agent in elastomeric, thermoplastic or thermoset polymer composites is an area in which carbon nanotubes are predicted to have significant utility. However, utilization of carbon nanotubes in these applications has been hampered due to the general inability to reliably produce individualized carbon nanotubes and the ability to disperse the individualized carbon nanotubes in a polymer matrix. Bosnyak et al., in various patent applications (e.g., US 2012-0183770 A1 and US 2011-0294013 A1), have made discrete carbon nanotubes through judicious and substantially simultaneous use of oxidation and shear forces, thereby oxidizing both the inner and outer surface of the nanotubes, typically to approximately the same oxidation level on the inner and outer surfaces, resulting in individual or discrete tubes.

The present invention differs from those earlier Bosnyak et al. applications and disclosures. The present invention describes a composition of discrete, individualized carbon nanotubes having targeted, or selective, oxidation levels and/or content on the exterior and/or interior of the tube walls. Such novel carbon nanotubes can have little to no inner tube surface oxidation, or differing amounts and/or types of oxidation between the tubes' inner and outer surfaces. These new discrete tubes are useful in many applications, including plasticizers, which can then be used as an additive in compounding and formulation of elastomeric, thermoplastic and thermoset composite for improvement of mechanical, electrical and thermal properties.

One embodiment of the present invention is a composition comprising a plurality of discrete carbon nanotubes, wherein the discrete carbon nanotubes comprise an interior and exterior surface, each surface comprising an interior surface oxidized species content and an exterior surface oxidized species content, wherein the interior surface oxidized species content differs from the exterior surface oxidized species content by at least 20%, and as high as 100%, preferably wherein the interior surface oxidized species content is less than the exterior surface oxidized species content.

The interior surface oxidized species content can be up to 3 weight percent relative to carbon nanotube weight, preferably from about 0.01 to about 3 weight percent relative to carbon nanotube weight, more preferably from about 0.01 to about 2, most preferably from about 0.01 to about 1. Especially preferred interior surface oxidized species content is from zero to about 0.01 weight percent relative to carbon nanotube weight.

The exterior surface oxidized species content can be from about 1 to about 6 weight percent relative to carbon nanotube weight, preferably from about 1 to about 4, more preferably from about 1 to about 2 weight percent relative to carbon nanotube weight. This is determined by comparing the exterior oxidized species content for a given plurality of nanotubes against the total weight of that plurality of nanotubes.

The interior and exterior surface oxidized species content totals can be from about 1 to about 9 weight percent relative to carbon nanotube weight.

Another embodiment of the invention is a composition comprising a plurality of discrete carbon nanotubes, wherein the discrete carbon nanotubes comprise an interior and exterior surface, each surface comprising an interior surface and an exterior surface oxidized species content, wherein the interior surface oxidized species content comprises from about 0.01 to less than about 1 percent relative to carbon nanotube weight and the exterior surface oxidized species content comprises more than about 1 to about 3 percent relative to carbon nanotube weight.

The discrete carbon nanotubes of either composition embodiment above preferably comprise a plurality of open ended tubes, more preferably the plurality of discrete carbon nanotubes comprise a plurality of open ended tubes. The discrete carbon nanotubes of either composition embodiment above are especially preferred wherein the inner and outer surface oxidation difference is at least about 0.2 weight percent.

The compositions described herein can be used as an ion transport. Various species or classes of compounds/drugs/chemicals which demonstrate this ion transport effect can be used, including ionic, some non-ionic compounds, hydrophobic or hydrophilic compounds.

The new carbon nanotubes disclosed herein are also useful in ground water remediation.

The compositions comprising the novel discrete targeted oxidized carbon nanotubes and also be used as a component in, or as, a sensor.

The compositions disclosed herein can also be used as a component in, or as, drug delivery or controlled release formulations.

In some embodiments, the compositions disclosed herein can be used as a component in, or as, payload molecule delivery or drug delivery or controlled release formulations. In particular various drugs, including small molecule therapeutics, peptides, nucleic acids, or combinations thereof may be loaded onto nanotubes and delivered to specific locations. Discrete carbon nanotubes may be used to help small molecules/peptides/nucleic acids that are cell membrane impermeable or otherwise have difficulty crossing the cell membrane to pass through the cell membrane into the interior of a cell. Once the small molecule/peptide/nucleic acid has crossed the cell membrane, it may become significantly more effective. Small molecules are defined herein as having a molecular weight of about 500 Daltons or less.

The pro-apoptotic peptide KLAKLAK is known to be cell membrane impermeable. By loading the peptide onto discrete carbon nanotubes KLAKLAK is able to cross the cell membrane of LNCaP human prostate cancer cells and trigger apoptosis. The KLAKLAK-discrete carbon nanotube construct can lead to the apoptosis of up to 100% of targeted LNCaP human prostate cancer cells. Discrete carbon nanotubes may also be useful for delivering other small molecules/peptides/nucleic acids across the cell membranes of a wide variety of other cell types. Discrete carbon nanotubes may be arranged to have a high loading efficiency, thereby enabling the delivery of higher quantities of drugs or peptides. In some instances, this transport across the cell membrane may be accomplished without the need for targeting or permeation moieties to aid or enable the transport. In other instances, the discrete carbon nanotubes may be conjugated with a targeting moiety (ex. peptide, chemical ligand, antibody) in order to assist with the direction of a drug or small molecule/peptide/nucleic acid towards a specific target. Discrete carbon nanotubes alone are well tolerated and do not independently trigger apoptosis.

Peptides, small molecules, and nucleic acids and other drugs may be attached to the exterior of the discrete carbon nanotubes via Van der Waals, ionic, or covalent bonding. As discussed, the level of oxidation may be controlled in order to promote a specific interaction for a given drug or small molecule/peptide/nucleic acid. In some instances, drugs or peptides that are sufficiently small may localize to the interior of discrete carbon nanotubes. The process for filling the interior or discrete carbon nanotubes may take place at many temperatures, including at or below room temperature. In some instances, the discrete carbon nanotubes may be filled to capacity in as little as 60 minutes with both small and large molecule drugs.

The payload molecule can be selected from the group consisting of a drug molecule, a radiotracer molecule, a radiotherapy molecule, diagnostic imaging molecule, fluorescent tracer molecule, a protein molecule, and combinations thereof.

Exemplary types of payload molecules that may be covalently or non-covalently associated with the discrete functionalized carbon nanotubes disclosed herein may include, but are not limited to, proton pump inhibitors, H2-receptor antagonists, cytoprotectants, prostaglandin analogues, beta blockers, calcium channel blockers, diuretics, cardiac glycosides, antiarrhythmics, antianginals, vasoconstrictors, vasodilators, ACE inhibitors, angiotensin receptor blockers, alpha blockers, anticoagulants, antiplatelet drugs, fibrinolytics, hypolipidemic agents, statins, hypnotics, antipsychotics, antidepressants, monoamine oxidase inhibitors, selective serotonin reuptake inhibitors, antiemetics, anticonvulsants, anxiolytic, barbiturates, stimulants, amphetamines, benzodiazepines, dopamine antagonists, antihistamines, cholinergics, anticholinergics, emetics, cannabinoids, 5-HT antagonists, NSAIDs, opioids, bronchodilator, antiallergics, mucolytics, corticosteroids, beta-receptor antagonists, anticholinergics, steroids, androgens, antiandrogens, growth hormones, thyroid hormones, anti-thyroid drugs, vasopressin analogues, antibiotics, antifungals, antituberculous drugs, antimalarials, antiviral drugs, antiprotozoal drugs, radioprotectants, chemotherapy drugs, cytostatic drugs, and cytotoxic drugs such as paclitaxel.

Batteries comprising the compositions disclosed herein are also useful. Such batteries include lithium, nickel cadmium, or lead acid types.

Formulations comprising the compositions disclosed herein can further comprise an epoxy, a polyurethane, or an elastomer. Such formulations can be in the form of a dispersion. The formulations can also include nanoplate structures.

The compositions can further comprise at least one hydrophobic material in contact with at least one interior surface.

The present invention relates to a composition comprising a plurality of discrete carbon nanotubes and a plasticizer wherein the discrete carbon nanotubes have an aspect ratio of 10 to about 500, and wherein the carbon nanotubes are functionalized with oxygen species on their outermost wall surface. The discrete carbon nanotubes comprise an interior and exterior surface, each surface comprising an interior surface and exterior surface oxidized species content wherein the interior surface oxidized species content comprises from about 0.01 to less than about 1 percent relative to carbon nanotube weight and the exterior surface oxidized species content comprises more than about 1 to about 3 percent relative to carbon nanotube weight. The oxygen species can comprise carboxylic acids, phenols, or combinations thereof.

The composition can further comprise a plasticizer selected from the group consisting of dicarboxylic/tricarboxylic esters, timellitates, adipates, sebacates, maleates, glycols and polyethers, polymeric plasticizers, bio-based plasticizers and mixtures thereof. The composition can comprise plasticizers comprising a process oil selected from the group consisting of naphthenic oils, paraffin oils, paraben oils, aromatic oils, vegetable oils, seed oils, and mixtures thereof.

The composition can further comprise a plasticizer selected from the group of water immiscible solvents consisting of but not limited to zylene, pentane, methylethyle ketone, hexane, heptane, ethyl actetate, ethers, diclorometh-ane, dichloroethane, cyclohexane, chloroform, carbon tetrachloride, butyl acetate butanol, benzene or mixtures thereof.

In yet another embodiment the composition is further comprises an inorganic filler selected from the group consisting of silica, nano-clays, carbon black, graphene, glass fibers, and mixtures thereof.

In another embodiment the composition is in the form of free flowing particles.

In another embodiment, the composition comprises a plurality of discrete carbon nanotubes and a plasticizer wherein the discrete carbon nanotubes comprise from about 10 weight percent to about 90 weight percent, preferably 10 weight percent to 40 weight percent, most preferably 10 to 20 weight percent.

An another embodiment is a process to form a composition comprising discrete carbon nanotubes in a plasticizer comprising the steps of: a) selecting a plurality of discrete carbon nanotubes having an average aspect ratio of from about 10 to about 500, and an oxidative species content total level from about 1 to about 15% by weight, b) suspending the discrete carbon nanotubes in an aqueous medium (water) at a nanotube concentration from about 1% to about 10% by weight to form an aqueous medium/nanotube slurry, c) mixing the carbon nanotube/aqueous medium (e.g., water) slurry with at least one plasticizer at a temperature from about 30° C. to about 100° C. for sufficient time that the carbon nanotubes migrate from the water to the plasticizer to form a wet nanotube/plasticizer mixture, e) separating the water from the wet carbon nanotube/plasticizer mixture to form a dry nanotube/plasticizer mixture, and f) removing residual water from the dry nanotube/plasticizer mixture by drying from about 40° C. to about 120° C. to form an anhydrous nanotube/plasticizer mixture.

Another embodiment is the composition of discrete carbon nanotubes in a plasticizer further mixed with a least one rubber. The rubber can be natural or synthetic rubbers and is preferably selected from the from the group consisting of natural rubbers, polyisobutylene, polybutadiene and styrene-butadiene rubber, butyl rubber, polyisoprene, styrene-isoprene rubbers, styrene-isoprene rubbers, ethylene, propylene diene rubbers, silicones, polyurethanes, polyester-polyethers, hydrogenated and non-hydrogenated nitrile rubbers, halogen modified elastomers, flouro-elastomers, and combinations thereof.

Another embodiment is the composition of discrete carbon nanotubes in a plasticizer further mixed with at least one thermoplastic polymer or at least one thermoplastic elastomer. The thermoplastic can be selected from but is not limited to acrylics, polyamides, polyethylenes, polystyrenes, polycarbonates, methacrylics, phenols, polypropylene, polyolefins, such as polyolefin plastomers and elastomers, EPDM, and copolymers of ethylene, propylene and functional monomers.

Yet another embodiment is the composition of discrete carbon nanotubes in a plasticizer further mixed with at least one thermoset polymer, preferably an epoxy, or a polyurethane. The thermoset polymers can be selected from but is not limited to epoxy, polyurethane, or unsaturated polyester resins.

For a more complete understanding of the present disclosure, and the advantages thereof, reference is now made to the following descriptions describing specific embodiments of the disclosure.

DETAILED DESCRIPTION OF THE INVENTION

In the following description, certain details are set forth such as specific quantities, sizes, etc., so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not.

Functionalized carbon nanotubes of the present disclosure generally refer to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof. In some embodiments, the carbon nanotubes may be functionalized before, during and after being exfoliated.

In various embodiments, a plurality of carbon nanotubes is disclosed comprising single wall, double wall or multi wall carbon nanotube fibers having an aspect ratio of from about 10 to about 500, preferably from about 40 to about 200, and an overall (total) oxidation level of from about 1 weight percent to about 15 weight percent, preferably from about 1 weight percent to about 10 weight percent, more preferably from about 1 weight percent to 5 weight percent, more preferably from about 1 weight percent to 3 weight percent. The oxidation level is defined as the amount by weight of oxygenated species covalently bound to the carbon nanotube. The thermogravimetric method for the determination of the percent weight of oxygenated species on the carbon nanotube involves taking about 7-15 mg of the dried oxidized carbon nanotube and heating at 5° C./minute from 100 degrees centigrade to 700 degrees centigrade in a dry nitrogen atmosphere. The percentage weight loss from 200 to 600 degrees centigrade is taken as the percent weight loss of oxygenated species. The oxygenated species can also be quantified using Fourier transform infra-red spectroscopy, FTIR, particularly in the wavelength range 1730-1680 $cm^{-1}$.

The carbon nanotubes can have oxidation species comprising carboxylic acid or derivative carbonyl containing species and are essentially discrete individual nanotubes, not entangled as a mass. Typically, the amount of discrete carbon nanotubes after completing the process of oxidation and shear is by a far a majority (that is, a plurality) and can be as high as 70, 80, 90 or even 99 percent of discrete carbon nanotubes, with the remainder of the tubes still partially entangled in some form. Complete conversion (i.e., 100 percent) of the nanotubes to discrete individualized tubes is most preferred. The derivative carbonyl species can include phenols, ketones, quaternary amines, amides, esters, acyl halogens, monovalent metal salts and the like, and can vary between the inner and outer surfaces of the tubes.

For example, one type of acid can be used to oxidize the tubes exterior surfaces, followed by water washing and the induced shear, thereby breaking and separating the tubes. If desired, the formed discrete tubes, having essentially no (or zero) interior tube wall oxidation can be further oxidized with a different oxidizing agent, or even the same oxidizing agent as that used for the tubes' exterior wall surfaces at a different concentration, resulting in differing amounts—and/or differing types—of interior and surface oxidation.

As-made carbon nanotubes using metal catalysts such as iron, aluminum or cobalt can retain a significant amount of the catalyst associated or entrapped within the carbon nanotube, as much as five weight percent or more. These residual metals can be deleterious in such applications as electronic devices because of enhanced corrosion or can interfere with the vulcanization process in curing elastomer composites. Furthermore, these divalent or multivalent metal ions can associate with carboxylic acid groups on the carbon nanotube and interfere with the discretization of the carbon nanotubes in subsequent dispersion processes. In other embodiments, the oxidized carbon nanotubes comprise a residual metal concentration of less than about 10000 parts per million, ppm, and preferably less than about 5000 parts per million. The metals can be conveniently determined using energy dispersive X-ray spectroscopy or thermogravimetric methods.

The composition of discrete carbon nanotubes in a plasticizer can be used as an additive to a variety of compounds and composites to improve the mechanical properties, thermal and electrical conductivity. An example is as an additive in rubber compounds used to fabricate rubber components in oil field applications such as seals, blowout preventers and drill motors with improved wear resistance, tear strength and thermal conductivity. Another example is as an additive in rubber compounds used to fabricate tires, seals and vibration dampeners. By selecting the appropriate plasticizer the additive has utility in compounding and formulating in thermoplastics, thermosets and composites.

As manufactured carbon nanotubes are in the form of bundles or entangled agglomerates and can be obtained from different sources, such as CNano Technology, Nanocyl, Arkema, and Kumho Petrochemical, to make discrete carbon nanotubes. An acid solution, preferably nitric acid solution at greater than about 60 weight % concentration, more preferably above 65% nitric acid concentration, can be used to prepare the carbon nanotubes. Mixed acid systems (e. g. nitric and sulfuric acid) as disclosed in US 2012-0183770 A1 and US 2011-0294013 A1, the disclosures of which are incorporated herein by reference, can be used to produce discrete, oxidized carbon nanotubes from as-made bundled or entangled carbon nanotubes.

General Process to Produce Discrete Carbon Nanotubes Having Targeted Oxidation

A mixture of 0.5% to 5% carbon nanotubes, preferably 3%, by weight is prepared with CNano grade Flotube 9000 carbon nanotubes and 65% nitric acid. While stirring, the acid and carbon nanotube mixture is heated to 70 to 90 degrees C. for 2 to 4 hours. The formed oxidized carbon nanotubes are then isolated from the acid mixture. Several methods can be used to isolate the oxidized carbon nanotubes, including but not limited to centrifugation, filtration, mechanical expression, decanting and other solid-liquid separation techniques. The residual acid is then removed by washing the oxidized carbon nanotubes with an aqueous medium such as water, preferably deionized water, to a pH of 3 to 4. The carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of 106 to 108 Joules/m$^3$. Equipment that meet this specification includes but is not limited to ultrasonicators, cavitators, mechanical homogenizers, pressure homogenizers and microfluidizers (Table 1). One such homogenizer is shown in U.S. Pat. No. 756,953, the disclosure of which is incorporated herein by reference. After shear processing, the oxidized carbon nanotubes are discrete and individualized carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized.

Another illustrative process for producing discrete carbon nanotubes follows: A mixture of 0.5% to 5% carbon nanotubes, preferably 3%, by weight is prepared with CNano Flotube 9000 grade carbon nanotubes and an acid mixture that consists of 3 parts by weight of sulfuric acid (97% sulfuric acid and 3% water) and 1 part by weight of nitric acid (65-70 percent nitric acid). The mixture is held at room temperature while stirring for 3-4 hours. The formed oxidized carbon nanotubes are then isolated from the acid mixture. Several methods can be used to isolate the oxidized carbon nanotubes, including but not limited to centrifugation, filtration, mechanical expression, decanting and other solid-liquid separation techniques. The acid is then removed by washing the oxidized carbon nanotubes with an aqueous medium, such as water, preferably deionized water, to a pH of 3 to 4. The oxidized carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of 106 to 108 Joules/m$^3$. Equipment that meet this specification includes but is not limited to ultrasonicators, cavitators mechanical homogenizers, pressure homogenizers and microfluidizers (Table 1). After shear and/or cavitation processing, the oxidized carbon nanotubes become oxidized, discrete carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized.

Example 1: Entangled Oxidized as MWCNT-3 Hour (oMWCNT-3)

One hundred milliliters of >64% nitric acid is heated to 85 degrees C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85 degrees for 3 hours and is labeled "oMWCNT-3". At the end of the reaction period, the oMWCNT-3 are filtered to remove the acid and washed with reverse osmosis (RO) water to pH of 3-4. After acid treatment, the carbon nanotubes are still entangled balls. The tubes are dried at 60° C. to constant weight.

Example 2: Entangled Oxidized as MWCNT-6 Hour (oMWCNT-6)

One hundred milliliters of >64% nitric acid is heated to 85 degrees C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85 degrees for 6 hours and is labeled "oMWCNT-6". At the end of the reaction period, the oMWCNT-6 are filtered to remove the acid and washed with reverse osmosis (RO) water to pH of 3-4. After acid treatment, the carbon nanotubes are still entangled balls. The tubes are dried at 60° C. to constant weight.

Example 3: Discrete Carbon Nanotube—Oxidize Outermost Wall (out-dMWCNT)

In a vessel, 922 kilograms of 64% nitric acid is heated to 83° C. To the acid, 20 kilograms of as received, multi-walled carbon nanotubes (C9000, CNano Technology) is added. The mixture is mixed and kept at 83° C. for 3 hours. After the 3 hours, the acid is removed by filtration and the carbon nanotubes washed with RO water to pH of 3-4. After acid treatment, the carbon nanotubes are still entangled balls with few open ends. While the outside of the tube is oxidized forming a variety of oxidized species, the inside of the nanotubes have little exposure to acid and therefore little oxidization. The oxidized carbon nanotubes are then suspended in RO water at a concentration of 1.5% by weight. The RO water and oxidized tangled nanotubes solution is subjected to intensely disruptive forces generated by shear (turbulent) and/or cavitation with process equipment capable of producing energy densities of $10^6$ to $10^8$ Joules/m$^3$. The resulting sample is labeled "out-dMWCNT" which represents outer wall oxidized and "d" as discrete. Equipment that meet this shear includes but is not limited to ultrasonicators, cavitators, mechanical homogenizers, pressure homogenizers, and microfluidizers (Table 1). It is believed that the shear and/or cavitation processing detangles and discretizes the oxidized carbon nanotubes through mechanical means that result in tube breaking and opening of the ends due to breakage particularly at defects in the CNT structure which is normally a 6 member carbon rings. Defects happen at places in the tube which are not 6 member carbon rings. As this is done in water, no oxidation occurs in the interior surface of the discrete carbon nanotubes.

Example 4: Discrete Carbon Nanotube—Oxidized Outer and Inner Wall (outlin-dMWCNT)

To oxidize the interior of the discrete carbon nanotubes, 3 grams of the out-dMWCNT is added to 64% nitric acid heated to 85° C. The solution is mixed and kept at temperature for 3 hours. During this time, the nitric acid oxidizes the interior surface of the carbon nanotubes. At the end of 3 hours, the tubes are filtered to remove the acid and then washed to pH of 3-4 with RO water. This sample is labeled "out/in-dMWCNT" representing both outer and inner wall oxidation and "d" as discrete.

Oxidation of the samples of carbon nanotubes is determined using a thermogravimetric analysis method. In this example, a TA Instruments Q50 Thermogravimetric Analyzer (TGA) is used. Samples of dried carbon nanotubes are ground using a vibration ball mill. Into a tared platinum pan of the TGA, 7-15 mg of ground carbon nanotubes are added. The measurement protocol is as follows. In a nitrogen environment, the temperature is ramped from room temperature up to 100° C. at a rate of 10° C. per minute and held at this temperature for 45 minutes to allow for the removal of residual water. Next the temperature is increased to 700° C. at a rate of 5° C. per minute. During this process the weight percent change is recorded as a function of temperature and time. All values are normalized for any change associated with residual water removal during the 100° C. isotherm. The percent of oxygen by weight of carbon nanotubes (% Ox) is determined by subtracting the percent weight change at 600° C. from the percent weight change at 200° C.

A comparative table (Table 2 below) shows the levels of oxidation of different batches of carbon nanotubes that have been oxidized either just on the outside (Batch 1, Batch 2, and Batch 3), or on both the outside and inside (Batch 4). Batch 1 (oMWCNT-3 as made in Example 1 above) is a batch of entangled carbon nanotubes that are oxidized on the outside only when the batch is still in an entangled form (Table 2, first column). Batch 2 (oMWCNT-6 as made in Example 2 above) is also a batch of entangled carbon nanotubes that are oxidized on the outside only when the batch is still in an entangled form (Table 2, second column). The average percent oxidation of Batch 1 (2.04% Ox) and Batch 2 (2.06% Ox) are essentially the same. Since the difference between Batch 1 (three hour exposure to acid) and Batch 2 (six hour exposure to acid) is that the carbon nanotubes were exposed to acid for twice as long a time in Batch 2, this indicates that additional exposure to acid does not increase the amount of oxidation on the surface of the carbon nanotubes.

Batch 3 (Out-dMWCNT as made in Example 3 above) is a batch of entangled carbon nanotubes that were oxidized on the outside only when the batch was still in an entangled form (Table 2, third column). Batch 3 was then been made into a discrete batch of carbon nanotubes without any further oxidation. Batch 3 serves as a control sample for the effects on oxidation of rendering entangled carbon nanotubes into discrete nanotubes. Batch 3 shows essentially the same average oxidation level (1.99% Ox) as Batch 1 and Batch 2. Therefore, Batch 3 shows that detangling the carbon nanotubes and making them discrete in water opens the ends of the tubes without oxidizing the interior.

Finally, Batch 4 (Out/In-dMWCNT as made in this Example 4 herein) is a batch of entangled carbon nanotubes that are oxidized on the outside when the batch is still in an entangled form, and then oxidized again after the batch has then been made into a discrete batch of carbon nanotubes (Table 2, fourth column). Because the discrete carbon nanotubes are open ended, in Batch 4 acid enters the interior of the tubes and oxidizes the inner surface. Batch 4 shows a significantly elevated level of average oxidation (2.39% Ox) compared to Batch 1, Batch 2 and Batch 3. The significant elevation in the average oxidation level in Batch 4 represents the additional oxidation of the carbon nanotubes on their inner surface. Thus, the average oxidation level for Batch 4 (2.39% Ox) is about 20% higher than the average oxidation levels of Batch 3 (1.99% Ox). In Table 2 below, the average value of the oxidation is shown in replicate for the four batches of tubes. The percent oxidation is within the standard deviation for Batch 1, Batch 2 and Batch 3.

TABLE 1

| Homogenizer Type | Flow Regime | Energy Density (J-m$^{-3}$) |
|---|---|---|
| Stirred tanks | turbulent inertial, turbulent viscous, laminar viscous | $10^3$-$10^6$ |
| Colloid mil | laminar viscous, turbulent viscous | $10^3$-$10^8$ |
| Toothed - disc disperser | turbulent viscous | $10^3$-$10^8$ |
| High pressure homogenizer | turbulent inertial, turbulent viscous, cavitation inertial, laminar viscous | $10^6$-$10^8$ |
| Ultrasonic probe | cavitation inertial | $10^6$-$10^8$ |
| Ultrasonic jet | cavitation inertial | $10^6$-$10^8$ |
| Microfluidization | turbulent inertial, turbulent viscous | $10^6$-$10^8$ |
| Membrane and mircochannel | Injection spontaneous transformation based | Low $10^3$ |

Excerpted from *Engineering Aspects of Food Emulsification and Homogenization*, ed. M. Rayner and P. Dejmek, CRC Press, New York 2015.

TABLE 2

Percent oxidation by weight of carbon nanotubes.

| Batch 1: oMWCNT-3 % Ox | Batch 2: oMWCNT-6 % Ox | Batch 3: Out- dMWCNT % Ox | Batch 4: Out/In- dMWCNT % Ox | Difference in % Ox (Batch 4- Batch 3) | *% difference in % Ox (Batch 4 v Batch 3) |
|---|---|---|---|---|---|
| 1.92 | 1.94 | 2.067 | 2.42 | 0.353 | 17% |
| 2.01 | 2.18 | 1.897 | 2.40 | 0.503 | 26.5% |

TABLE 2-continued

Percent oxidation by weight of carbon nanotubes.

|  | Batch 1: oMWCNT-3 % Ox | Batch 2: oMWCNT-6 % Ox | Batch 3: Out-dMWCNT % Ox | Batch 4: Out/In-dMWCNT % Ox | Difference in % Ox (Batch 4-Batch 3) | *% difference in % Ox (Batch 4 v Batch 3) |
|---|---|---|---|---|---|---|
|  | 2.18 | NM | 2.12 | 2.36 | 0.24 | 11% |
|  | 2.05 | NM | 1.85 | NM | n/a | n/a |
| Average | 2.04 | 2.06 | 1.99 | 2.39 | 0.4 | 20% |
| St. Dev. | 0.108 | 0.169 | 0.130 | 0.030 | n/a | n/a |

NM = Not Measured
*% difference between interior and exterior oxidation surfaces (Batch 4 v Batch 3) = (((outside % oxidation) − (inside % oxidation)) ÷ (outside % oxidation)) × 100

An illustrative process to form a composition comprising discrete carbon nanotubes in a plasticizer is to first select a plurality of discrete carbon nanotubes having an average aspect ratio of from about 10 to about 500, and an oxidative species content total level from about 1 to about 15% by weight. Then the discrete carbon nanotubes are suspended using shear in water at a nanotube concentration from about 1% to about 10% by weight to form the nanotube water slurry. The slurry is then mixed with at least one plasticizer at a temperature from about 30° C. to about 100° C. for sufficient time that the carbon nanotubes migrate from the water to the plasticizer to form a water nanotube/plasticizer mixer. The mixture can comprise from 70% to about 99.9% water. The bulk of the water is separated from the mixture by filtration, decanting or other means of mechanical separation. The filtered material can contain from about 50% to about 10% water. The filtered material is then dried at a temperature from about 40° C. to about 120° C. to form an anhydrous nanotube/plasticizer mixture with less than 3% water, most preferably less than 0.5% water by weight and for some applications 0% water by weight.

Example 5

A concentrate of discrete carbon nanotubes in water with only the exterior wall oxidized as in Example 3 is diluted to a 2% by weight in deionized water. The slurry is heated to 40° C. while stirring with an overhead stirrer at 400 rpm. For every gram of discrete carbon nanotubes, 4 grams of TOTM (trioctyl trimellitate) from Sigma Aldrich is added to the stirring mixture. For 4 hours, the mixture is stirred at 750 rpm and kept at 40° C. During this time, the oil and discrete carbon nanotubes floats to the top, leaving clear water at the bottom. When this occurs, the water is separated from the TOTM/carbon nanotube mixture by filtration. The TOTM and discrete carbon nanotubes are dried in a forced air convection oven at 70° C. until residual water is removed. The result is a flowable powder. The concentration of discrete carbon nanotubes is determined by thermogravimetric means and found to be 20% discrete carbon nanotubes and 80% TOTM.

Example 6

The discrete carbon nanotubes and plasticizer composition of Example 5 comprising 20% discrete carbon nanotubes and 80% TOTM (trioctyle trimellitate) is added at concentrations of 2 parts per hundred resin (phr) and 3 parts per hundred resin (phr) to a nitrile rubber formulation (Table 3). The oil concentration of the compounds is adjusted to compensate for the additional oil from the composition of this invention. The compound is then cured into plaques for testing. Constrained tear testing is performed using an Instron tensiometer. Constrained tear samples are punched out using a die, making a rectangle 1.5 inches by 1 inch by 1 inch with a specimen-centered notch ½ inch long, sliced perpendicular to the longest dimension. The specimen is gripped equal distance from the notch and pulled by the Instron. Shear strain and stress is recorded and the area under the stress-strain curve from strain zero to the final failure is measured. This area is the total tear energy. The results in Table 4 indicate that an increase in tear strength is imparted by the discrete carbon nanotubes.

TABLE 3

| Ingredient | Control | 2 phr dCNT | 3 phr dCNT |
|---|---|---|---|
| Nitrile Rubber (Nipol 3640S) | 100 | 100 | 100 |
| 20% dCNT in TOTM | 0 | 10 | 15 |
| N774 Carbon Black | 80 | 75 | 75 |
| Polyester sebacate plasticizer (Paraplex G-25) | 15 | 7 | 3 |
| Coumarone Indene Resin (Cumar P25) | 10 | 10 | 10 |
| Stearic Acid | 1 | 1 | 1 |
| Zinc Oxide (Kadox 911) | 5 | 5 | 5 |
| Antioxidant (Vanox CDPA) | 2 | 2 | 2 |
| Antioxidant (Santoflex 6PPD) | 2 | 2 | 2 |
| High molecular fatty acid esters (Struktol WB212) | 2 | 2 | 2 |
| Accelerator DTDM | 2 | 2 | 2 |
| Accelerator (Morfax) | 2.26 | 2.26 | 2.26 |
| Accelerator TMTM | 1 | 1 | 1 |

TABLE 4

| Description | Constrained Tear (psi) |
|---|---|
| Control | 482 |
| 2 phr dCNT | 537 |
| 3 phr dCNT | 574 |

Example 7

The discrete carbon nanotubes and plasticizer composition of Example 5 comprising 20% discrete carbon nanotubes and 80% TOTM (trioctyle trimellitate) is added at concentrations 3 parts per hundred resin (phr) to a nitrile rubber formulation (Table 5). The oil concentration of the compound is adjusted to compensate for the additional oil from the composition of this invention so that all formulations have equivalent oil concentrations. A comparative compound is prepared with carbon nanotubes as received (Flotube C9000, CNano) (Table 5). Carbon black content is adjusted so that the measured hardness is the same for the three samples. The Shore A hardness is 67 for the control and 67 for the 3 phr CNT of this invention and 68 for the 3 phr "As is" carbon nanotubes (C9000). The constrained tear is measured as described in Example 6. The discrete carbon nanotubes and oil composition (dCNT) of this invention have higher total tear energy than the entangled carbon nanotubes (C9000) and the control. The tear energy of entangled carbon nanotubes, C9000, is worse than the control. (Table 6)

TABLE 5

| Ingredient | Control | 3 phr dCNT | 3 phr C9000 |
|---|---|---|---|
| Nitrile Rubber (Nipol 3640S) | 100 | 100 | 100 |
| 20% dCNT in TOTM | 0 | 15 | 0 |
| MWCNT as received (C9000, CNano) | 0 | 0 | 3 |
| N774 Carbon Black | 80 | 75 | 75 |
| Polyester sebacate plasticizer (Paraplex G-25) | 15 | 3 | 15 |
| Coumarone Indene Resin (Cumar P25) | 10 | 10 | 10 |
| Stearic Acid | 1 | 1 | 1 |
| Zinc Oxide (Kadox 911) | 5 | 5 | 5 |
| Antioxidant (Vanox CDPA) | 2 | 2 | 2 |
| Antioxidant (Santoflex 6PPD) | 2 | 2 | 2 |
| High molecular fatty acid esters (Struktol WB212) | 2 | 2 | 2 |
| Accelerator DTDM | 2 | 2 | 2 |
| Accelerator (Morfax) | 2.26 | 2.26 | 2.26 |
| Accelerator TMTM | 1 | 1 | 1 |

TABLE 6

| Description | Constrained Tear (psi) |
|---|---|
| Control | 482 |
| 3 phr dCNT | 574 |
| 3 phr C9000 | 394 |

It is known to those practiced in the art that the addition of filler to a rubber compound will increase the viscosity of the compound. Unexpectedly, the addition of discrete carbon nanotube and oil mixture from Example 7 did not increase the viscosity but instead decreased viscosity, while the entangled carbon nanotubes of Example 7 (C9000) increased the viscosity. The viscosity is measured using a Mooney Rheometer at 125° C. The initial viscosity measured is descriptive of the processibility of the compound. The compound containing the discrete carbon nanotubes of this invention and described in Example 7 is found to be equal to the control while the compound containing the entangled carbon nanotubes (C9000) is found to be higher than the control (Table 7).

TABLE 7

| Description | Minimum Mooney Viscosity ML(1 + 30) |
|---|---|
| Control | 23.1 |
| 3 phr dCNT | 23.1 |
| 3 phr C9000 | 26.6 |

Disclosed embodiments may also relate to a composition useful for treating and/or remediating contaminated soil, groundwater and/or wastewater by treating, removing, modifying, sequestering, targeting labeling, and/or breaking down at least a portion of any dry cleaning compounds and related compounds such as perchloroethene (PCE), trichloroethene (TCE), 1,2-dichloroethene (DCE), vinyl chloride, and/or ethane. Embodiments may also relate to compounds useful for treating, removing, modifying, sequestering, targeting labeling, and/or breaking down at least a portion of any oils, hazardous or undesirable chemicals, and other contaminants. Disclosed embodiments may comprise a plurality of discrete carbon nanotubes, wherein the discrete carbon nanotubes comprise an interior and exterior surface. Each surface may comprise an interior surface oxidized species content and/or an exterior surface oxidized species content. Embodiments may also comprise at least one degradative or otherwise chemically active molecule that is attached on either the interior or the exterior surface of the plurality of discrete carbon nanotubes. Such embodiments may be used in order to deliver known degrative and/or chemically active molecules to the location of any contaminated soil, groundwater and/or wastewater.

Addition of Payload Molecule

Aqueous solubility of drug substances is an important parameter in pre-formulation studies of a drug product. Several drugs are sparingly water-soluble and pose challenges for formulation and dose administration. Organic solvents or oils and additional surfactants to create dispersions can be used. If the payload molecule is easily dissolved or dispersed in an aqueous media, the filter cake need not be dried. If the payload molecule is not easily dissolved or dispersed in aqueous media, the filter cake is first dried at 80° C. in vacuo to constant weight. The payload molecule in the liquid media at the desired concentration is added to the discrete carbon nanotubes and allowed several hours to equilibrate within the tube cavity. The mixture is then filtered to form a cake, less than about 1 mm thickness, then the bulk of the payload solution not residing within the tubes are removed by high flow rate filtration. The rate of filtration is selected so that little time is allowed for the payload molecules to diffuse from the tube cavity. The filter cake plus payload drug is then subjected to an additional treatment if desired to attach a large molecule such an aqueous solution of a biopolymer, an amino acid, protein or peptide.

Example 8

A calibration curve for the UV absorption of niacin as a function of the concentration of niacin in water was determined. A solution was prepared by mixing 0.0578 grams of discrete functionalized carbon nanotubes of this invention with 0.0134 grams of niacin in 25 ml of water [0.231 grams niacin/gram of carbon nanotube]. The tubes were allowed to settle and an aliquot of the fluid above the tubes removed hourly. The UV-vis absorption of this aliquot was measured and the resulting amount of niacin in the solution recorded. The amount of niacin in solution stabilized after 6 hours. A final sample was taken 20 hours after mixing. The difference between the amounts of niacin remaining in the solution and the original amount was determined to be the amount of niacin associated with the discrete functionalized carbon nanotubes. It was found that 0.0746 grams of niacin associated with each gram of carbon nanotubes. The total amount of niacin absorbed by the carbon nanotubes was 0.0043 grams. Assuming an average carbon nanotube length of 1000 nm, external diameter of 12 nm and internal diameter of 5 nm, the available volume within the tube is 0.093 cm3 per gram of carbon nanotubes. Since the density of niacin is 1.473 g/cm3, then the maximum amount of niacin that can fit in the tubes is 0.137 grams. Therefore, the measured absorption of 0.0746 g niacin/g CNT amount could be confined to the interior of the tube.

Example 9

A poly (vinyl alcohol), PVOH, is sufficiently large (30 kDa-70 kDa) that it cannot be absorbed internally in a carbon nanotube. PVOH is used as a surfactant for carbon nanotubes because it associates and wraps the exterior of the carbon nanotube. In this experiment, PVOH was added to a mixture of 0.0535 g of carbon nanotubes and 0.0139 g niacin (0.26 grams niacin to 1 gram carbon nanotubes) in 25 ml water. This was allowed to rest overnight. Using the UV-vis technique of Example 1, the amount of niacin associated with the carbon nanotubes was determined to be 0.0561 grams niacin per gram of carbon nanotubes, less than the 0.0746 grams in example 1. The total amount of niacin absorbed was 0.003 grams.

Calculations were made assuming carbon nanotube length of 1000 nm, external diameter of 12 nm and internal diameter of 5 nm. Given the density of PVOH is 1.1 g/cm3 and the ratio of PVOH to carbon nanotubes was 0.23 to 1, the average layer thickness of PVOH on the carbon nanotube is 0.6 nm. Therefore there is sufficient PVOH to encapsulate the carbon nanotube and displace any niacin on the surface of the tube and the measured amount of 0.0561 grams of niacin per gram of carbon nanotubes is in the interior of the carbon nanotube.

In another example the discrete functionalized carbon nanotubes can be dispersed in a polymeric matrix, for example polyethylene oxide, in the melt or in a solution and the payload molecule added.

TABLE 8

Lengths (nm)

| | Condition 1 | Condition 2 | Condition 3 |
|---|---|---|---|
| Mean | 424 | 487 | 721 |
| Standard Error | 25.3 | 34.9 | 50 |
| Median | 407 | 417.0 | 672 |
| Standard Deviation | 177 | 281 | 315 |
| Sample Variance | 31461 | 79108 | 99418 |
| Kurtosis | −0.83 | 1.5 | −0.02 |
| Skewness | 0.03 | 1.2 | 0.64 |
| Range | 650 | 1270.0 | 1364 |
| Minimum | 85 | 85.0 | 161 |
| Maximum | 735 | 1355 | 1525 |

Condition 1 is an example of a narrow distribution with low mean length.
Condition 2 is an example of broad distribution with low mean length.
Condition 3 is an example of high mean length and broad distribution.

To determine tube lengths, a sample of tubes is diluted in isopropyl alcohol and sonicated for 30 minutes. It is then deposited onto a silica wafer and images are taken at 15 kV and 20,000× magnification by SEM. Three images are taken at different locations. Utilizing the JEOL software (included with the SEM) a minimum of 2 lines are drawn across on each image and measure the length of tubes that intersect this line.

Skewness is a measure of the asymmetry of a probability distribution. A positive value means the tail on the right side of the distribution histogram is longer than the left side and vice versa. Positive skewness is preferred which indicates means more tubes of long lengths. A value of zero means a relatively even distribution on both sides of the mean value. Kurtosis is the measure of the shape of the distribution curve and is generally relative to a normal distribution. Both skewness and kurtosis are unitless.

The following table shows representative values of discrete carbon nanotubes diameters: Table 9: Diameter (unrelated to condition above)

TABLE 9

Diameter (unrelated to condition above)

| | | | |
|---|---|---|---|
| Mean diameter (nm*) | | 12.5 | |
| Median diameter (nm) | | 11.5 | |
| Kurtosis | 3.6 | | |
| Skewness | 1.8 | | |
| Calculated aspect ratio (L/D) | 34 | 39 | 58 |

*nm = nanometer

A small sample of the filter cake is dried in vacuum at 100° C. for 4 hours and a thermogravimetric analysis performed at 10° C./min heating rate in nitrogen from 100° C. to 600° C. The amount of oxidized species on the fiber is taken as the weight loss between 200 and 600° C. The dispersion of individual tubes (discrete) is also determined by UV spectroscopy. Water is added to the wet cake to give a 0.5% weight carbon nanotube suspension, then sodium dodecylbenzene sulfonic acid is added at a concentration of 1.5 times the mass of oxidized carbon nanotubes. The solution is sonicated for 30 minutes using a sonicator bath then diluted to a concentration of 2.5×10-5 g carbon nanotubes/ml. The carbon nanotubes will give a UV absorption at 500 nm of at least 1.2 absorption units.

The improvement in flow processibility of the compositions can be determined using a rheometer, for example, utilizing concentric cylinders with a well-defined geometry to measure a fluid's resistance to flow and determine its viscous behavior. While relative rotation of the outer cylinder causes the composition to flow, its resistance to deformation imposes a shear stress on the inner wall of the cup, measured in units of Pa.

Embodiments

Embodiments disclosed in this application include:
1. A composition comprising a plurality of discrete carbon nanotubes, wherein the discrete carbon nanotubes comprise an interior and exterior surface, each surface comprising an interior surface oxidized species content and an exterior surface oxidized species content, wherein the interior surface oxidized species content differs from the exterior surface oxidized species content by at least 20%, and as high as 100%.
2. The composition of embodiment 1 wherein the interior surface oxidized species content is less than the exterior surface oxidized species content.
3. The composition of embodiment 1 wherein the interior surface oxidized species content is up to 3 weight percent relative to carbon nanotube weight, preferably from about 0.01 to about 3 weight percent relative to carbon nanotube weight, more preferably from about 0.01 to about 2, most preferably from about 0.01 to about 1.
4. The composition of embodiment 1 wherein the exterior surface oxidized species content is from about 1 to about 6 weight percent relative to carbon nanotube weight, preferably from about 1 to about 4, more preferably from about 1 to about 2.
5. The composition of embodiment 1 wherein the interior and exterior surface oxidized species content totals from about 1 to about 9 weight percent relative to carbon nanotube weight.

6. A composition comprising a plurality of discrete carbon nanotubes, wherein the discrete carbon nanotubes comprise an interior and exterior surface, each surface comprising an interior surface and an exterior surface oxidized species content, wherein the interior surface oxidized species content comprises from about 0.01 to less than about 1 percent relative to carbon nanotube weight and the exterior surface oxidized species content comprises more than about 1 to about 3 percent relative to carbon nanotube weight.

7. The composition of embodiment 6 wherein the discrete carbon nanotubes comprise a plurality of open ended tubes.

8. The composition of embodiment 6 wherein the plurality of discrete carbon nanotubes comprise a plurality of open ended tubes.

9. The composition of embodiment 1 wherein the discrete carbon nanotubes comprise a plurality of open ended tubes.

10. Use of the composition of embodiment 1 as an ion transport.

11. Use of the composition of embodiment 1 as targeting, sequestering and labeling agent in ground water remediation.

12. A sensor comprising the composition of embodiment 1 or embodiment 6.

13. A drug delivery or controlled release formulation comprising the composition of embodiment 1 or embodiment 6.

14. A battery comprising the composition of embodiment 1 or embodiment 6.

15. A formulation comprising the composition of embodiment 1 or embodiment 6 further comprising an epoxy, a polyurethane, or an elastomer.

16. The composition of embodiment 1 or embodiment 6 further comprising at least one hydrophobic material in contact with at least one interior surface.

17. The composition of embodiment 1 or embodiment 6 wherein the inner and outer surface oxidation difference is at least about 0.2 weight percent.

18. The composition of embodiment 1 or embodiment 6 and at least one plasticizer, wherein the discrete carbon nanotubes have an aspect ratio of about 10 to about 500, and wherein the carbon nanotubes have an oxidation level of about 1 to 3 percent by weight of carbon nanotubes.

19. The composition of embodiment 18 wherein the composition comprises from about 10 weight percent to about 90 weight, preferably from about 10 weight percent to about 40 weight percent, discrete carbon nanotubes.

20. The composition of embodiment 18 wherein the oxygenated species is selected from the group consisting of carboxylic acids, phenols, aldehydes, ketones, ether linkages, and combinations thereof.

21. The composition of embodiment 18 wherein the total oxygenated species content of the interior surface and exterior surface comprises from about 1% to 15% by weight of the carbon nanotubes.

22. The composition of embodiment 18, wherein the plasticizer is selected from the group consisting of dicarboxylic/tricarboxylic esters, timellitates, adipates, sebacates, maleates, glycols and polyethers, polymeric plasticizers, bio-based plasticizers, and mixtures thereof.

23. The composition of embodiment 18, wherein the plasticizer is a process oil selected from the group consisting of naphthenic oils, paraffin oils, paraben oils, aromatic oils, vegetable oils, seed oils, and mixtures thereof.

24. The composition of embodiment 23 having a viscosity about the same as, or less than, an identical composition comprising the same elements in the same ratios, except the carbon nanotubes are not discrete but are entangled as-manufactured.

25. The composition of embodiment 18, wherein the plasticizer is a water immiscible solvent selected from the group consisting of xylene, pentane, methylethyl ketone, hexane, heptane, ethyl actetate, ethers, dicloromethane, dichloroethane, cyclohexane, chloroform, carbon tetrachloride, butyl acetate butanol, benzene, and mixtures thereof.

26. The composition of embodiment 18, further comprising an inorganic filler selected from the group consisting of silica, nano-clays, carbon black, graphene, glass fibers, and mixtures thereof.

27. The composition of embodiment 18 in the form of free flowing particles.

28. A process to make the composition of embodiment 18, comprising the steps of: a) selecting a plurality of discrete carbon nanotubes having an average aspect ratio of from about 10 to about 500, and an oxidative species content total level from about 1 to about 15% by weight, b) suspending the discrete carbon nanotubes in an aqueous medium at a nanotube concentration from about 1% to about 10% by weight to form an aqueous medium/nanotube slurry, c) mixing the carbon nanotube/aqueous medium slurry with at least one plasticizer at a temperature from about 30° C. to about 100° C. for sufficient time that the carbon nanotubes migrate from the aqueous medium to the plasticizer to form a wet nanotube/plasticizer mixture, e) separating the aqueous medium from the wet carbon nanotube/plasticizer mixture to form a dry nanotube/plasticizer mixture, and f) removing residual aqueous medium from the dry nanotube/plasticizer mixture by drying from about 40° C. to about 120° C. to form an anhydrous nanotube/plasticizer mixture.

29. The composition of embodiment 18, wherein the composition is further mixed with at least one rubber.

30. The composition of embodiment 29, wherein the rubber is a natural or synthetic rubber selected from the group consisting of natural rubbers, polyisobutylene, polybutadiene and styrene-butadiene rubber, butyl rubber, polyisoprene, styrene-isoprene rubbers, styrene-isoprene rubbers, ethylene, propylene diene rubbers, silicones, polyurethanes, polyester-polyethers, hydrogenated and non-hydrogenated nitrile rubbers, halogen modified elastomers, fluoro-elastomers, and combinations thereof.

31. The composition of embodiment 18, wherein the composition further comprises at least one thermoplastic polymer, at least one thermoplastic elastomer, or combinations thereof.

32. The composition of embodiment 18, wherein the composition further comprises at least one thermoset polymer, preferably epoxy, or polyurethane.

33. A composition useful for treating groundwater that has been contaminated with dry-cleaning compounds comprising a plurality of discrete carbon nanotubes, wherein the discrete carbon nanotubes comprise an interior and exterior surface, each surface comprising an interior surface oxidized species content and an exterior surface oxidized species content, and at least one degradative molecule that is attached on the interior or exterior surface of the plurality of discrete carbon nanotubes.

We claim:

1. A composition comprising a plurality of discrete multiwall carbon nanotubes, wherein the discrete multiwall carbon nanotubes comprise an interior and exterior sidewall surface, the interior sidewall surface comprising an interior surface oxidized species content and the exterior sidewall surface comprising an exterior surface oxidized species content, wherein the interior surface oxidized species content is at least about 0.01 weight percent relative to carbon nanotube weight and differs from the exterior surface oxidized species content by at least 20%, and as high as 100%.

2. The composition of claim 1 wherein the plurality of discrete carbon nanotubes comprises a plurality of open ended tubes.

3. The composition of claim 1 wherein the interior surface oxidized species content is less than the exterior surface oxidized species content.

4. The composition of claim 1 wherein the interior surface oxidized species content is up to 3 weight percent relative to carbon nanotube weight.

5. The composition of claim 1 wherein the exterior surface oxidized species content is from about 1 to about 6 weight percent relative to carbon nanotube weight.

6. The composition of claim 1 wherein the interior and exterior surface oxidized species content totals from about 1 to about 9 weight percent relative to carbon nanotube weight.

7. The composition of claim 1 wherein the oxygenated species is selected from the group consisting of carboxylic acids, phenols, aldehydes, ketones, ether linkages, and combinations thereof.

8. The composition of claim 1 wherein the total oxygenated species content of the interior surface and exterior surface comprises from about 1% to 15% by weight of the carbon nanotubes.

9. The composition of claim 1 in the form of free flowing particles.

10. The composition of claim 1, wherein the composition is further mixed with at least one rubber.

11. The composition of claim 1, wherein the composition further comprises at least one thermoplastic polymer, at least one thermoplastic elastomer, or combinations thereof.

12. The composition of claim 1, wherein the composition further comprises at least one thermoset polymer selected from the group consisting of an epoxy, a polyurethane, and combinations thereof.

* * * * *